United States Patent [19]

Schubart

[11] Patent Number: 5,245,076

[45] Date of Patent: Sep. 14, 1993

[54] PROCESS FOR THE PREPARATION OF β-HALOGENO-TERT.-ALKYL ISOCYANATES

[75] Inventor: Rüdiger Schubart, Bergisch Gladbach, Fed. Rep. of Germany

[73] Assignee: Bayer Aktiengesellschaft, Leverkusen, Fed. Rep. of Germany

[21] Appl. No.: 862,049

[22] Filed: Apr. 2, 1992

[30] Foreign Application Priority Data

Apr. 12, 1991 [DE] Fed. Rep. of Germany ....... 4111904

[51] Int. Cl.$^5$ ............................................ C07C 263/04
[52] U.S. Cl. .................................... 560/349; 560/356
[58] Field of Search ................................ 560/349, 356

[56] References Cited

U.S. PATENT DOCUMENTS

| | | | |
|---|---|---|---|
| 3,277,137 | 10/1966 | Powers | 560/349 X |
| 3,535,360 | 10/1970 | Holtschmidt et al. | 560/349 |
| 4,257,974 | 3/1981 | Koenig et al. | 560/349 |
| 4,344,891 | 8/1982 | Koenig et al. | 560/349 X |
| 4,439,369 | 3/1984 | Koenig et al. | 560/349 X |

FOREIGN PATENT DOCUMENTS

| | | |
|---|---|---|
| 620028 | 1/1963 | Belgium . |
| 0037481 | 10/1981 | European Pat. Off. . |
| 0425768 | 6/1967 | Switzerland . |
| 1353680 | 5/1974 | United Kingdom . |

OTHER PUBLICATIONS

Gorbatenko et al, 1007 *Synthesis*, Feb., (1980), No. 2, Stuttgart, pp. 85-110.

*Primary Examiner*—José G. Dees
*Assistant Examiner*—Vera C. Clarke
*Attorney, Agent, or Firm*—Sprung Horn Kramer & Woods

[57] ABSTRACT

The invention relates to a process for the preparation of known β-halogeno-tert.-alkyl isocyanates of the formula

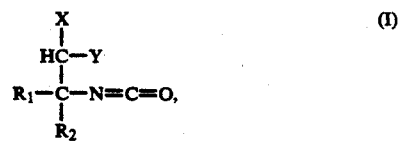

in which
X represents chlorine,
Y represents hydrogen or chlorine,
R$_1$ represents in each case straight-chain or branched alkyl or halogenoalkyl and
R$_2$ represents in each case straight-chain or branched alkyl, halogenoalkyl or optionally halogen- and/or trifluoromethyl-substituted phenyl, where tert.-alkyl isocyanates of the formula (II)

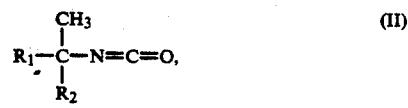

in which
R$_1$ and R$_2$ have the meaning given above, are converted to the corresponding tert.-alkylcarbamoyl chlorides by means of hydrogen chloride gas, these are reacted with elemental chlorine under irradiation or in the presence of catalysts, and finally the β-halogeno-tert.-alkyl isocyanates are liberated by dehydrohalogenation at elevated temperature.

7 Claims, No Drawings

PROCESS FOR THE PREPARATION OF β-HALOGENO-TERT.-ALKYL ISOCYANATES

The invention relates to a new process for the preparation of known β-halogeno-tert.-alkyl isocyanates, which can be used as intermediates for the synthesis of rubber additives or of biologically active compounds, such as for example herbicides (cf. for example EP-A 294 666).

It is already known that β-monochloro-tert.-alkyl isocyanates are obtained when β-hydroxy-tert.-alkylamines are first converted to β-chloro-tert.-alkylamine hydrochlorides using thionyl chloride, and these are then converted to the isocyanates using phosgene (cf. DE-OS (German Published Specification) 2 045 906).

The poor yields of the chlorinated tert.-alkyl isocyanates are a disadvantage of this process.

It is further already known (cf. Houben-Weyl volume E4, page 1171) to react methyl isocyanate with chlorine under irradiation. However, in this way, the polychlorinated chlorocarbonyl-isocyanide-dichloride is obtained.

It is further known from the literature that HCl addition products of isocyanates have a tendency to fragment (cf. Houben-Weyl volume E4, page 63).

For example, further addition of hydrogen chloride to N-tert.-butyl-N-vinylcarbamoyl chloride causes the elimination of the tert.-butyl moiety as tert.-butyl chloride.

An obvious conclusion is that the chlorination of tert.-alkylcarbamoyl chlorides must also lead to the elimination of tert.-alkyl chlorides. Moreover, there are indications in the literature that at temperatures of about 200° C. and above the elimination of the chlorocarbonyl group as phosgene is to be expected. [cf. Angew. Chem. 74, 848 (1962)].

It has now been found that β-halogeno-tert.-alkyl isocyanates of the formula (I)

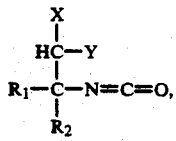

in which
X represents chlorine,
Y represents hydrogen or chlorine,
$R_1$ represents in each case straight-chain or branched alkyl or halogenoalkyl and
$R_2$ represents in each case straight-chain or branched alkyl, halogenoalkyl or optionally halogen- and/or trifluoromethyl-substituted phenyl,
are obtained in good yields and high purity, when tert.-alkyl isocyanates of the formula (II)

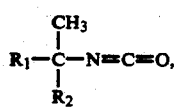

in which
$R_1$ and $R_2$ have the meaning given above,
are first converted, by the introduction of HCl gas, to the corresponding tert.-alkylcarbamoyl chlorides, which are then reacted with elemental chlorine, optionally under irradiation, optionally in the presence of catalysts and optionally in suitable solvents, in a suitable conventional laboratory apparatus at temperatures between −20° C. and +50° C., at atmospheric pressure or a slight overpressure of up to 2000 mbar. The desired monochloro-tert.-alkyl isocyanates are finally obtained by heating the reaction solution, hydrogen chloride again being liberated.

It is highly surprising that this chlorination procedure gives the desired β-halogeno-tert.-alkyl isocyanates of the formula (I) in good yields. On account of the references from the literature cited above, elimination of the tert.-alkyl moiety in the form of tert.-alkyl chloride (cf. Houben-Weyl vol. E4 p. 63) and especially fragmentations during the reaction of isocyanates or their HCl adducts, the carbamoyl chlorides, was rather to be expected (cf. Houben-Weyl 4/56 Photochemie I and II, 891–892).

The process according to the invention is preferably used to obtain compounds of the formula (I) in which $R_1$ represents methyl, ethyl, n- or iso-propyl, n-, iso-, sec.- or tert.-butyl, $R_2$ represents methyl, ethyl, n- or iso-propyl, n-, iso-, sec.- or tert.-butyl, or phenyl which is optionally mono- to trisubstituted by identical or different substituents from the series comprising fluorine, chlorine, bromine and/or trifluoromethyl, especially preferably $R_1$ represents methyl or ethyl and $R_2$ methyl, ethyl or phenyl, in particular methyl.

The process according to the invention is very particularly preferably used to prepare compounds of the formula (I) in which X represents chlorine and Y represents hydrogen, i.e. β-monochlorinated tert.-alkyl isocyanates.

The process according to the invention may, in the case of the use of tert.-butyl isocyanate, be described by the following reaction scheme:

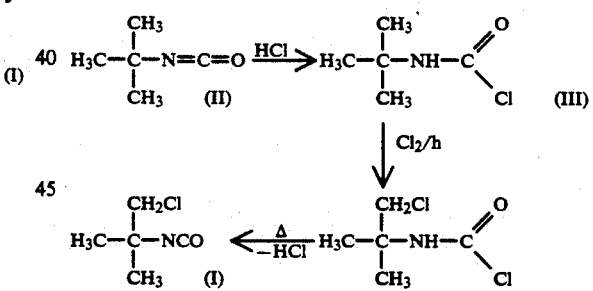

The process according to the invention can be carried out as a "one-pot" reaction in the absence or presence of diluents. All diluents customary for such halogenation reactions can be used, such as for example dichloromethane, chloroform or tetrachloromethane. Tetrachloromethane is preferably used.

The process according to the invention is preferably carried out with addition of diluents. The process according to the invention can optionally be carried out under irradiation or by addition of suitable catalysts.

Irradiation can be carried out for example with a water-cooled high-pressure mercury vapour lamp, where the halogenation lamp can be used either as an immersion lamp or mounted externally. In mounting the lamp, care must be taken that as much light as possible reaches the halogenation zone. All high-pressure mercury vapour lamps conventionally used for such halogenations may be used for the process according to the invention. Naturally, other lamps suitable for such halogenations may also be used.

The catalysts used are preferably peroxides, such as for example cumyl peroxide or benzoyl peroxide, in the usual concentrations.

The reaction temperatures can be varied within a wide range when carrying out the process according to the invention. Generally, the temperatures employed are between −20° C. and 60° C., preferably between 0° C. and 50° C., especially preferably room temperatures.

The process according to the invention can be carried out at atmospheric pressure or at an overpressure of up to 2000 mbar. Atmospheric pressure is generally employed.

For carrying out the process, hydrogen chloride gas is passed into a mixture of tert.-alkyl isocyanate and tetrachloromethane in a conventional laboratory apparatus up to saturation.

Then, when the monohalogenated compounds of the formula (I) are to be obtained (i.e. X=chlorine and Y=hydrogen), generally stoichiometric amounts or an excess, preferably up to 1.2 mol, and especially preferably 1.1 mol, of chlorine are added per mole of tert.-alkyl isocyanate of the formula (II), or, after HCl addition, tert.-alkylcarbamyl chloride of the formula (III).

If the process is carried out in the presence of catalysts, then generally 0.001 to 1.5 mol %, preferably 0.02 to 1 mol % and especially preferably 0.1 to 0.5 mol %, of catalyst is used per mole of tert.-alkyl isocyanate of the formula (II), or tert.-alkylcarbamoyl chloride of the formula (III).

This process of batch halogenation, after a preceding hydrohalogenation, can be described as a "one-pot" process, and is generally carried out to a conversion of 40 to 80%, preferably 45 to 65%, especially preferably 50 to 55%.

The advantage of this procedure is that the proportion of by-products and thus the loss of material (i.e. loss of starting material of the formula (II)) is markedly lower.

In this way the yield of β-halogeno-tert.-alkyl isocyanate from a given quantity of tert.-alkyl isocyanate can be markedly improved.

This process also allows the possibility of the chlorination of a mixture of tert.-alkyl isocyanate using tert.-alkylcarbamoyl chloride, as can occur for example on incomplete hydrochlorination of tert.-alkyl isocyanate in the first stage, or when the chlorination of the tert.-alkyl isocyanate is begun without previous hydrohalogenation, and only the resulting hydrogen chloride leads to formation of the tert.-carbamoyl chloride.

EXAMPLE 500 g (∼5 mol) of tert.-butyl isocyanate in 500 ml of tetrachloromethane are saturated with hydrogen chloride gas at about 10° C. Chlorine gas is then passed into the reaction solution and the mixture is chlorinated at 20° to 32° C. under irradiation with a high-pressure mercury vapour lamp, which is immersed in the reaction medium and cooled with water. The composition of the chlorination mixture immediately after completion of the chlorination is as follows (in area %), the determination being accomplished indirectly by gas chromatographic measurement of the fraction in each case of the corresponding isocyanate:

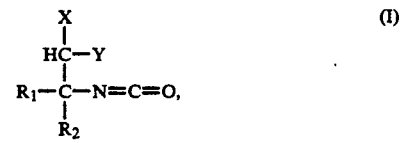

8% of the starting material and 5.6% of unknown by-products are also present.

After completion of the chlorination process, the reaction mixture is heated. This leads to expulsion of the dissolved hydrogen chloride, but also to the dehydrohalogenation of the dissolved tert.-butylcarbamoyl chlorides. Finally the tetrachloromethane is distilled off, and the mixture is heated up to a temperature of 120° C. At this point the process is interrupted, the mixture is allowed to cool and is then reheated, this time under vacuum.

By fine fractionation, 383 g of monochloro-tert.-butyl isocyanate (60% of theory) are obtained at a boiling point of 50° C. and 27.7 mbar, with recovered starting material being reused.

The two isomeric dichloro-tert.-butyl isocyanates, which can also be separated by distillation, remain in the pot.

It will be understood that the specification and examples are illustrative but not limitative of the present invention and that other embodiments within the spirit and scope of the invention will suggest themselves to those skilled in the art.

What is claimed is:

1. A process for the preparation of β-halogeno-tert.-alkyl isocyanates of the formula (I)

$$\begin{array}{c} X \\ | \\ HC-Y \\ | \\ R_1-C-N=C=O, \\ | \\ R_2 \end{array} \quad (I)$$

in which
  X represents chlorine,
  Y represents hydrogen or chlorine,
  $R_1$ represents in each case straight-chain or branched alkyl or halogenoalkyl and
  $R_2$ represents in each case straight-chain or branched alkyl, halogenoalkyl or optionally halogen- and/or trifluoromethyl-substituted phenyl,
said process comprising the following steps:
  (a) reacting a tert.-alkyl isocaynate of the formula (II):

$$\begin{array}{c} CH_3 \\ | \\ R_1-C-N=C=O, \\ | \\ R_2 \end{array} \quad (II)$$

in which
    $R_1$ and $R_2$ have the meaning given above,
    with hydrogen chloride gas to yield the corresponding tert.-alkylcarbamoyl chlorides;
  (b) chlorinating the tert.-alkylcarbamoyl chlorides by reaction with elemental chlorine under irradiation or in the presence of catalysts in a suitable apparatus to yield β-halogeno-tert.-alkylcarbamoyl chlorides; and (c) subjecting the β-halogen-tert.-alkylcarbamoyl chlorides to dehydrohalogenation to yield β-halogeno-tert.-alkyl isocyanates of the formula (I); steps (a), (b) and (c) being carried out at temperatures between about −20° C. and +50° C., at about atmospheric pressure or a slight overpressure of up to about 2000 mbar.

2. A process according to claim 1, wherein
$R_1$ represents methyl, ethyl, n- or iso-propyl, n-, iso-, sec.-, tert.-butyl and their monohalogenated derivatives, and $R_2$ represents methyl, ethyl, n- or iso-propyl, n-, iso-, sec.- or tert.-butyl and their monohalogenated derivatives or phenyl which is optionally mono- to trisubstituted by identical or different substituents from the series comprising fluorine, chlorine, bromine and/or trifluoromethyl.

3. A process according to claim 1, wherein
$R_1$ represents methyl or ethyl and $R_2$ represents methyl, ethyl or phenyl.

4. The process according to claim 1, wherein peroxides or azo compounds are used as catalysts.

5. The process according to claim 1, wherein the reaction is carried out as batch halogenation.

6. The process according to claim 5, wherein the reaction is interrupted at a conversion of 40 to 80%.

7. The process according to claim 1, wherein the whole process is carried out as a "one-pot" reaction.

* * * * *